(12) United States Patent
Ito et al.

(10) Patent No.: US 7,101,673 B2
(45) Date of Patent: Sep. 5, 2006

(54) METHOD FOR DETECTING A NUCLEIC ACID COMPRISING ASYMMETRICAL AMPLIFICATION

(75) Inventors: Seiichiro Ito, Tokyo (JP); Junko Tanoue, Tokyo (JP); Fumiko Yasukawa, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 11/007,353

(22) Filed: Dec. 9, 2004

(65) Prior Publication Data

US 2005/0158752 A1    Jul. 21, 2005

(30) Foreign Application Priority Data

Dec. 16, 2003   (JP) .............................. 2003-418323

(51) Int. Cl.
   *C12Q 1/68*   (2006.01)
(52) U.S. Cl. .......................... 435/6; 435/91.2; 435/91.1
(58) Field of Classification Search .................... None
   See application file for complete search history.

(56) References Cited

U.S. PATENT DOCUMENTS 5,314,809 A * 5/1994 Erlich et al. ............... 435/91.2
6,858,412 B1 * 2/2005 Willis et al. ............... 435/91.1

OTHER PUBLICATIONS

Ruano et al. ("Coupled amplification and sequencing of genomic DNA" Proc. Natl. Acad. Sci. Apr. 1991. vol. 88: pp. 2815-2819).*
Valentine et al. ("Detection of Helibacter pylori by Using the Polymerase Chain Reaction" Journal of Clinical Microbiology. Apr. 1991. vol. 29, No. 4: pp. 689-695).*
Deng et al. "Simulttaneous amplification and sequencing of genomic DNA (SAS): sequencing of 16S rRNA genes using total genomic DNA from *Butyrivibrio fibrisolvens*, and detection and genotyping of nonculturable mycoplamsa-like organisms directly from total DNA isolated from infected plants" Journal of Microbiological Methods. 1993. 17: pp. 103-113.*

\* cited by examiner

*Primary Examiner*—Kenneth R. Horlick
*Assistant Examiner*—Christopher M Babic
(74) *Attorney, Agent, or Firm*—Reed Smith LLP; Stanley P. Fisher, Esq.; Juan Carlos A. Marquez, Esq.

(57) ABSTRACT

A method for detecting amplified nucleic acid fragments is provided. The method comprises the steps of carrying out amplification reaction to amplify a predetermined region of a nucleic acid in a reaction solution comprising the nucleic acid as a template, a pair of primers, deoxynucleotides, and dideoxynucleotides; hybridizing the amplified products of the reaction solution to a probe; and then detecting the hybridization between the amplified products and the probe.

7 Claims, 5 Drawing Sheets

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
agcccagtca ccctttggtg                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
ctttgactgt gacagttttc                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
aggcatacac tgaagtgaaa                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
aggcatacac taaagtgaaa                                                  20

METHOD FOR DETECTING A NUCLEIC ACID COMPRISING ASYMMETRICAL AMPLIFICATION

FIELD OF THE INVENTION

The present invention relates to a method for detecting a nucleic acid that is obtained by amplification reaction.

BACKGROUND OF THE INVENTION

The genome is the blueprint of an organism, and in human, it is made up of about three billion pairs of deoxyribonucleotides (DNA). In the genomic sequence, multiple sites differing among individuals of the same species have been discovered, and these are called polymorphism. In particular, the polymorphism due to a single nucleotide substitution is called single nucleotide polymorphism (SNP). Variations in SNP may sometimes have influence on diseases and drug efficacy. Thus, SNP is paid attention to as a possible factor to explain differences among individuals.

From the genome, mRNA, rRNA, and tRNA are expressed, and specific proteins and the like are selectively synthesized from these blueprints, supporting life activities. Studies on the presence or absence of expression of these RNAs and on their sequences are also important to elucidate life phenomena. The sequences of rRNAs are partially different depending on species, and investigation of their sequences makes it possible to identify species, and so forth.

For these purposes, it is essential to amplify the target sequence as well as to detect the amplified product by labeling in order to acquire recognizable information. A general method for amplifying a nucleic acid sequence known at present is polymerase chain reaction (PCR). PCR represents an amplification reaction in which a pair of primers is designed to sandwich a region desired to be amplified from a template DNA sequence; a reaction solution containing these primers, dNTP serving as substrates, a thermostable DNA polymerase, and the like is prepared; and a reaction cycle of heat denaturation, annealing, and extension, carried out at different temperatures, is repeated 20 to 30 times to amplify the region.

As the method for labeling amplified products, there is a visualization method, after amplification, in which the presence or absence of amplification by PCR is examined by electrophoresis in agarose gel and subsequent dyeing of double-stranded DNA with ethidium bromide and the like. Further, detection using the principle of specific binding to complementary chain necessitates direct labeling such as incorporation of a fluorescent substance into amplified products. The direct method for labeling amplification products includes a method in which the amplification reaction is carried out by binding in advance a fluorescent label, biotin, or the like to a primer, and a method in which a substrate containing a radioisotope, labeled with a fluorophore, or bound with biotin is allowed to be incorporated into amplified products during amplification reaction.

Although PCR in principle is able to amplify a very minute quantity of a template DNA sequence to a large quantity, there are certain cases in practice where amplification reaction does not take place or an incorrect region is amplified. Particularly when a partial region of a genome is amplified, the quantity of the template DNA to be amplified is extremely small relative to the quantity of the total DNA. Owing to non-specific binding of primers under the circumstances, it frequently occurs that amplification reaction does not take place or an incorrect region is amplified, thus making it difficult to obtain the target amplification products.

The amplified DNA must be labeled in a certain way in order to acquire objective information. Since any method of labeling after PCR requires much expense in time and effort, expensive reagents such as enzyme, and the like, it is costly compared with a method of labeling during PCR amplification reaction. Particularly when a large number of samples must be processed, this cost gives rise to a problem. However, it is not actually easy to perform labeling during PCR amplification reaction as well as acquiring the amplified products from a genome or the like at the same time.

When the presence or absence of binding between labeled amplification products and a probe prepared to be complementary to the former to hybridize in a sequence-specific manner is detected, the amplification products do not continue to bind to the probe but eventually form stable double strands with their complementary chains of the amplified products because the amplification products are double-stranded by nature and present in excess in terms of the number of molecules. In other words, the detection sensitivity becomes very low when only a labeling substance is simply incorporated into the amplification products.

In an attempt to solve the problem by allowing amplified products to be biased toward formation of single-stranded DNA, an asymmetrical PCR method has been devised (reference; "PCR Method of Gene Amplification: Basics and New Developments", By Ikunosin Kato, Ed. Fujinaga, Kyoritsu Shuppan Co. Ltd., pp. 7–26 (Dec. 10, 1990)). In this method, a pair of primers for use in amplification reaction is supplied in unequal quantities rather than equal quantities. However, it is practically not easy to obtain amplification products stably from a genome and the like by the asymmetrical PCR method. Further, when the primers are present in excess even though present in unequal proportions, amplification reaction similar to an ordinary PCR occurs, and thus the problem was not solved.

SUMMARY OF THE INVENTION

Hence, the present invention has taken the above situation into account and aims to provide an entirely new method for labeling a nucleic acid that allows amplified nucleic acid fragments to be detected with high accuracy.

The present invention that has achieved the above aim includes the following:

1) A method for detecting a nucleic acid according to one aspect of the present invention comprises steps of carrying out amplification reaction to amplify a predetermined region of the nucleic acid in a reaction solution comprising the nucleic acid acting as a template, a pair of primers, deoxynucleotides, and dideoxynucleotides; hybridizing amplified products comprised in the reaction solution to a probe; and then detecting the hybridization between the amplified products and the probe.

2) The method for detecting a nucleic acid according to another aspect of the present invention is that the amplification reaction is carried out using a reaction solution in which the concentration ratio of the deoxynucleotides to the dideoxynucleotides meets the following equation:

$$0.1 < \{dNTP \text{ concentration}/(dNTP \text{ concentration} + ddNTP \text{ concentration})\}^{ab} < 1.0$$

(where "dNTP concentration" represents the concentration of deoxynucleotides in the reaction solution, and "ddNTP concentration" represents the concentration of dideoxynucleotides in the reaction solution. Further, a represents the number of nucleotides extended in the amplification reaction ($1 \leq a$), and b represents the cycle number of the amplification reaction in the above equation.)

3) The method for detecting a nucleic acid according to still another aspect of the present invention is that b in the equation is in the range of $20 \leq b \leq 24$.

4) The method for detecting a nucleic acid according to still another aspect of the present invention is that either one of the pair of primers is designed to anneal to a region adjacent to the nucleotide sequence complementary to the probe.

5) The method for detecting a nucleic acid according to still another aspect of the present invention is that at least one of the pair of primers and/or the probe is labeled in advance.

6) The method for detecting a nucleic acid according to still another aspect of the present invention is that the amplification reaction is carried out using the reaction solution that comprises at least one additional primer having a lower Tm value compared with each of the pair of primers.

7) The method for detecting a nucleic acid according to still another aspect of the present invention is that the temperature of annealing in the amplification reaction is set lower after each amplification cycle.

8) The method for detecting a nucleic acid according to still another aspect of the present invention is that the amplification reaction is carried out using the reaction solution that comprises a pair of secondary primers having lower Tm values compared with those of the pair of primers.

According to the present invention, the reaction solution after the amplification reaction contains single-stranded nucleic acids complementary to the region targeted for detection in the template nucleic acid, and therefore the region targeted for detection can be detected with high sensitivity.

DETAILED DESCRIPTION OF THE PREFERRED EMBODIMENTS

Figure 1:
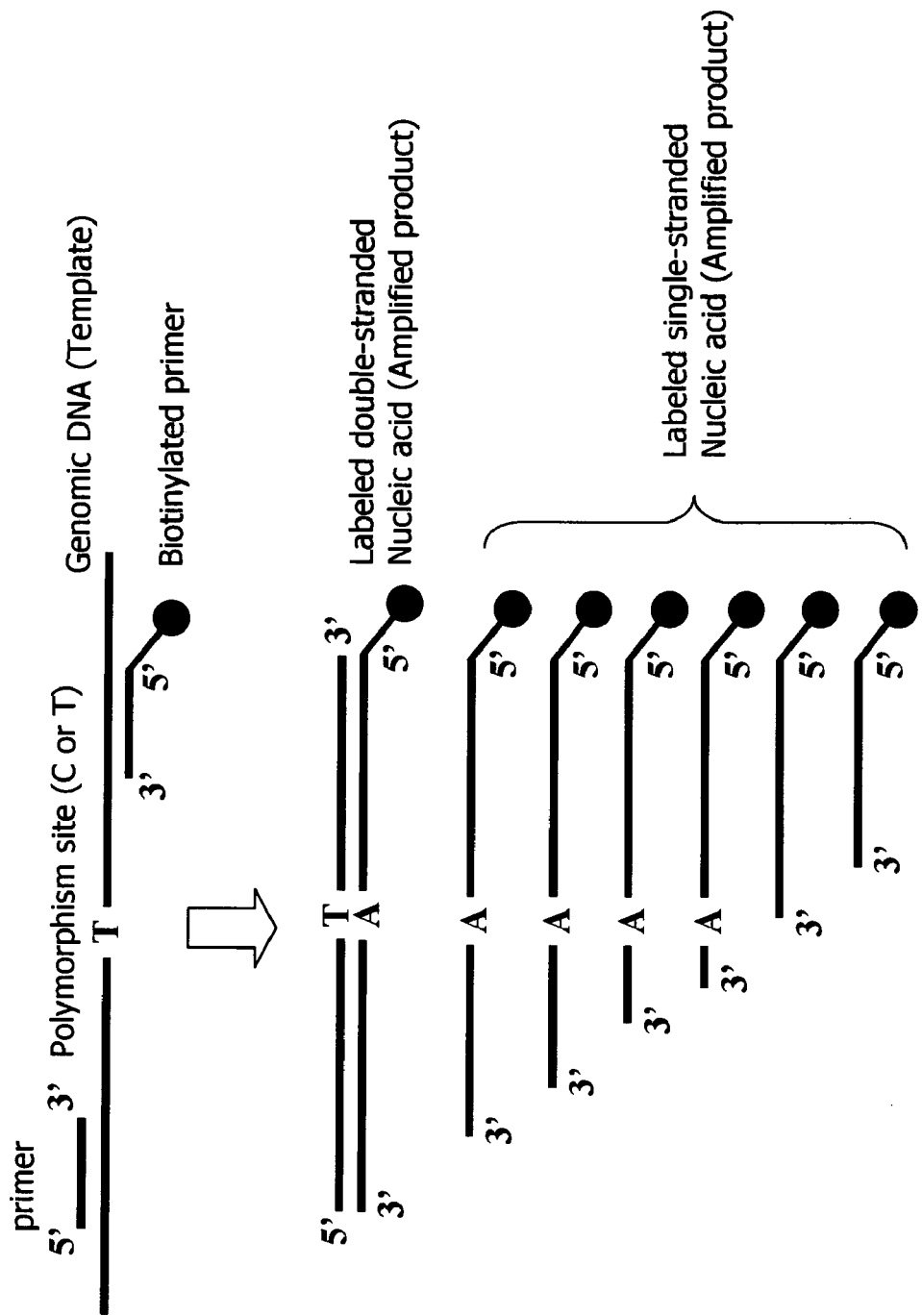
FIG. 1 is a schematic drawing to explain a step of carrying out an amplification reaction in a method for detecting a nucleic acid according to the present invention.

Hereinafter, a method for detecting a nucleic acid according to the present invention is explained in detail with reference to the accompanying drawings. It should be noted that the technical scope of the present invention is not limited to the explanations and examples described below. In other words, modifications that can be readily made by one of ordinary skill in the art even if not disclosed directly in the explanations and examples below are included in the technical scope of the present invention. For example, a method to label amplification products by the use of biotinylated primer is exemplified and explained in the explanation described below. However, a method in which primers labeled with other substances such as fluorophore are used and a method in which substrates labeled with a radioisotope or modified with a fluorophore are incorporated during the amplification reaction are also included in the technical scope of the present invention. In the examples explained below, only one primer of the pair of primers for use in PCR is biotinylated, thus resulting in labeling of only one strand of the amplified products. However, a method in which both strands are labeled by biotinylating both primers may also be included in the technical scope of the present invention.

First, the method for detecting a nucleic acid according to the present invention comprises the steps of carrying out amplification reaction to amplify a predetermined region of a nucleic acid in a reaction solution containing the nucleic acid acting as a template, a pair of primers, deoxynucleotides, and dideoxynucleotides; hybridizing amplified products contained in the reaction solution to a probe; and then detecting the hybridization between the amplified products and the probe. The presence or absence of the sequence complementary to the probe in the template nucleic acid can be detected in the step of detecting the hybridization. Hereinafter, the above steps are explained in order.

The step of carrying out amplification reaction is the one in which a predetermined region in the template nucleic acid is amplified and amplified products containing single-stranded nucleic acids are synthesized. For example, when a SNP is detected, the region containing the target SNP is amplified. Further, when the presence or absence of a gene is detected, the region containing the gene is amplified. In these cases, the nucleic acid acting as the template may be any one of DNA molecules such as genomic DNA, plasmid DNA, and cDNA synthesized by reverse transcription of mRNA, and RNA molecules such as mRNA, tRNA, and rRNA.

The pair of primers contained in the reaction solution is designed to sandwich the region of the amplification target described above. Particularly when the detection target is SNP or a specific region of a gene, it is preferred that one of the primers is designed to be adjacent to the site of the SNP or the specific region of the gene. Furthermore, it is desirable to label either primer of the pair or both of the primers. It should be noted that neither primer of the pair needs labeling when the probe is labeled as described later in detail.

Any conventionally-known labels can be used for these labeling. For example, the labels include biotin, fluorescent dyes, digoxigenin, and the like.

The reaction solution contains a nucleic acid polymerase to synthesize a chain complementary to the template nucleic acid. The nucleic acid polymerase is not particularly limited as long as it is generally used. For example, the nucleic acid polymerase includes DNA polymerase, reverse transcriptase, RNA polymerase, and the like. The use of a thermostable DNA polymerase derived from thermophilic bacteria or a high-fidelity DNA polymerase is preferred for the nucleic acid polymerase.

In the present step, deoxynucleotides and dideoxynucleotides serving as substrates for the nucleic acid polymerase contained in the reaction solution are included. That is, the nucleic acid polymerase uses deoxynucleotides as substrates when synthesizing a sequence complementary to the template nucleic acid. On the other hand, once dideoxynucleotides are incorporated into a growing polynucleotide chain by the nucleic acid polymerase, further extension reaction is terminated. In other words, the DNA polymerase is unable to carry out a further extension reaction whenever a dideoxynucleotide is incorporated during the synthesis of a sequence complementary to the template nucleic acid. Note here that deoxynucleotides represent triphosphate derivatives of deoxyadenosine (dATP), deoxyguanosine (dGTP), deoxythymidine (dTTP), and deoxycytidine (dCTP), respectively. Dideoxynucleotides represent triphosphate derivatives of dideoxyadenosine (ddATP), dideoxyguanosine (ddGTP), dideoxythymidine (ddTTP), and dideoxycytidine (ddCTP), respectively.

According to the present step, labeled double-stranded nucleic acids and labeled single-stranded nucleic acids can be obtained as amplification products by carrying out PCR using the reaction solution described above, as shown schematically in FIG. 1. The labeled single-stranded nucleic acids are amplified products, amplified by the extension reaction from the pre-labeled primer, which are unable to form stable double-stranded structures due to termination of the extension reaction caused by incorporating a dideoxynucleotide into the growing chain. It should be noted that the labeled double-stranded nucleic acid is an amplified product capable of forming a stable double-stranded structure because no dideoxynucleotide was incorporated during the extension reaction.

Following the step of carrying out amplification reaction described above, hybridization is performed using the reaction solution containing the amplified products and a probe prepared separately. The probe here means a nucleic acid construct including oligonucleotides that are appropriately designed when the method for detecting a nucleic acid according to the present invention is applied. For example, when SNP is detected, the probe is constructed such that a nucleic acid fragment containing either of the sequences with the SNP variation is included and bound to beads, the bottom surface of a dish, or the like. Further, for example, when the presence or absence of a specific gene is detected, the probe is constructed such that a nucleic acid fragment having a specific sequence of the gene is included and bound to beads, the bottom surface of a dish, or the like.

Figure 2:
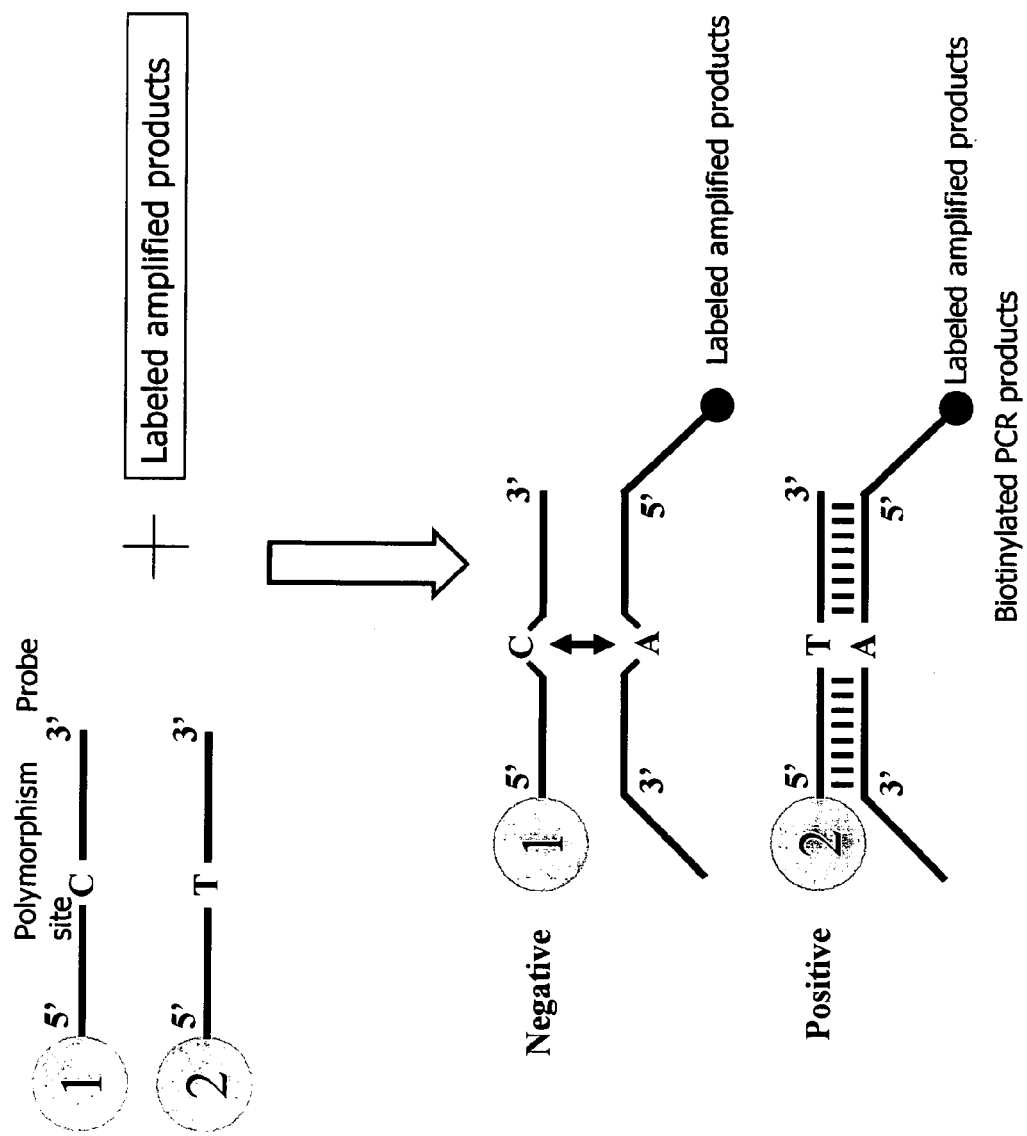
FIG. 2 is a schematic drawing to explain a step of carrying out hybridization in the method for detecting a nucleic acid according to the present invention.

To be more specific, a pair of probes that is constructed so as to include a nucleic acid fragment having a sequence with C or T at a polymorphism site and immobilized to beads is prepared as shown in FIG. 2. Here, a first probe with C at the polymorphism site and a second probe with T at the polymorphism site are prepared. When hybridization is carried out between the first probe or the second probe and the labeled amplified products, the amplified products hybridizes to either one of the first probe and the second probe depending on the polymorphism contained in the amplified products.

The conditions for hybridization are not particularly limited as long as a specific double-strand is formed and non-specific double strands are not formed. The conditions for the hybridization include, for example, those carried out in a solution of 3 M tetramethylammonium chloride (TMAC), 0.1% Sarkosyl, 50 mM Tris-HCl (pH 8.0), and 4 mM EDTA (pH 8.0) for 30 min (10 to 120 min) at 55 degrees C. (50 to 60 degrees C.). Washing after the hybridization may be performed using a solution having a composition similar to that of the above solution.

Next, the presence or absence of hybridization between the probe and the amplified products is detected based on a label of the amplified fragments. In the example shown in FIG. 2, the amplified products labeled with biotin have A at the polymorphism site, and thus hybridize to the second probe (probe with T at the polymorphism site). Accordingly, in this example, signals owing to biotin can be detected from beads immobilized with the second probe. In other words, the polymorphism of the amplified products can be identified, in this step, by detecting the label from either one of the first probe and the second probe.

Particularly in the present method, labeled single-stranded nucleic acids are contained in the reaction solution as the amplified products, as described above. These single-stranded nucleic acids are able to form stable double-strand structures with the probe. In contrast, when the double-stranded nucleic acid that is an amplified product is converted to single-stranded nucleic acids by heat denaturation and then subjected to a double-strand formation with the probe, double-stranded structure is more stably formed with the original complementary chain, being less stably formed with the probe. That is, one of the single-stranded nucleic acids generated by heat denaturation of the double-stranded nucleic acids forms double strand under competition between the probe and the other single-stranded nucleic acid. In this case, sensitivity of the detection is reduced significantly, and there is a possibility that identification of, for example, SNP genotype or the presence or absence of a specific gene by detection of a desired nucleic acid sequence cannot be carried out.

On the other hand, in the method for detecting a nucleic acid according to the present invention, single-stranded nucleic acids that cannot form stable double-stranded structures with the other single-stranded nucleic acid described above are produced in the reaction solution in the step of carrying out amplification reaction. Accordingly, the nucleic acid sequence of interest can be detected with high sensitivity according to the present method by hybridizing the single-stranded nucleic acids produced by the amplification reaction to the probe.

In the present method, when the presence ratio of dideoxynucleotides in the reaction solution is high, the amplification reaction does not proceed exponentially, and therefore enough amplified products cannot be produced, resulting in a failure of the detection. On the other hand, when the presence ratio of dideoxynucleotides is low, single-stranded nucleic acids that are amplified products mixed in the reaction solution become low, resulting in a failure of enhancement of the detection sensitivity. For these reasons, it is desirable that the amplification reaction described above is carried out by preparing the reaction solution so that the concentration ratio between the deoxynucleotides and the dideoxynucleotides meets the following equation:

$$0.1 \leq \{dNTP \text{ concentration}/(dNTP \text{ concentration} + ddNTP \text{ concentration})\}^{ab} < 1.0$$

(where "dNTP concentration" represents the concentration of deoxynucleotides in the above reaction solution, and "ddNTP concentration" represents the concentration of dideoxynucleotides in the above reaction solution. Further, a represents the number of nucleotides extended in the amplification reaction ($1 \leq a$), and b represents the cycle number of the amplification reaction in the above equation.)

The use of the reaction solution that meets the above equation makes it possible to amplify single-stranded nucleic acids without fail and achieve excellent detection sensitivity. In the reaction solution below the lower limit of the above equation, the proportion of double-stranded nucleic acids contained in the reaction solution after the amplification reaction becomes large, giving rise to a possibility that detection sensitivity becomes low. In the reaction solution beyond the upper limit of the above equation, the probability that the amplification reaction from a pair of primers is terminated at an early stage becomes high, giving rise to a possibility that single-stranded nucleic acids enough for the detection may not be amplified.

For example, the relations of changes in cycle numbers and chain lengths of extended nucleotides with changes in expected amplification rates when the proportions of dideoxynucleotides in the reaction solution are 1/1,000 and 5/10,000, respectively, are shown in Table I and Table II, respectively.

TABLE I

| Cycle number | 32-mer | 64-mer | 128-mer | 256-mer |
|---|---|---|---|---|
| 1 | 0.9685 | 0.9380 | 0.8798 | 0.7744 |
| 16 | 0.5991 | 0.3590 | 0.1289 | 0.0166 |
| 20 | 0.5271 | 0.2779 | 0.0772 | 0.0060 |
| 24 | 0.4638 | 0.2151 | 0.0463 | 0.0021 |

TABLE II

| Cycle number | 32-mer | 64-mer | 128-mer | 256-mer |
|---|---|---|---|---|
| 1 | 0.9841 | 0.9685 | 0.9380 | 0.8798 |
| 16 | 0.7741 | 0.5992 | 0.3591 | 0.1289 |
| 20 | 0.7261 | 0.5272 | 0.2779 | 0.0773 |
| 24 | 0.6811 | 0.4639 | 0.2152 | 0.0463 |

In the above Table I and Table II, the amplification rate is calculated assuming that the amount of amplification product to be obtained by the amplification reaction carried out in the reaction solution that does not contain dideoxynucleotides is one. It can be understood from these tables that the amplification rate drops sharply as the chain length to be extended becomes longer.

It is desirable that b in the above equation is in the range of from 20 to 24 ($20 \leq b \leq 24$). When the cycle number of the amplification reaction is in this range, rate-limiting of the amplification reaction caused by inactivation of the nucleic acid polymerase and the like can be avoided, and an optimal detection sensitivity can be achieved. For example, the cycle number of an ordinary PCR is not less than 20 (25–30 times). When the cycle number exceeds 20, amplification reaction becomes significantly slow owing to inactivation of a thermostable DNA polymerase and the like. For this reason, the cycle number should be desirably from 20 to 24. Expected amplification rates after predetermined cycles of amplification are shown in Table III where the amplification rates in the first cycle are set to be 0.9, 0.95, 0.96, 0.97, 0.98, and 0.99, respectively.

TABLE III

| Cycle number | 0.9 | 0.94 | 0.95 | 0.96 | 0.97 | 0.98 | 0.99 |
|---|---|---|---|---|---|---|---|
| 1 | 0.9000 | 0.9400 | 0.9500 | 0.9600 | 0.9700 | 0.9800 | 0.9900 |
| 16 | 0.1853 | 0.3716 | 0.4401 | 0.5204 | 0.6143 | 0.7238 | 0.8515 |
| 20 | 0.1216 | 0.2901 | 0.3585 | 0.4420 | 0.5438 | 0.6676 | 0.8179 |
| 24 | 0.0798 | 0.2265 | 0.2920 | 0.3754 | 0.4814 | 0.6158 | 0.7857 |

When the cycle numbers of 20 and 24 are paid attention to, the approximate amplification rates lie between 0.1 and 0.8, from which the equation below was derived.

$$0.9 < \{dNTP \text{ concentration}/(dNTP \text{ concentration} + ddNTP \text{ concentration})\}^a < 0.99$$

(where "dNTP concentration" represents the concentration of deoxynucleotides in the above reaction solution, and "ddNTP concentration" represents the concentration of dideoxynucleotides in the above reaction solution. Further, a represents the number of nucleotides extended in the amplification reaction ($1 \leq a$).)

When the amplification rate in the first cycle is from 0.95 to 0.96, single-stranded DNAs occupy 1.5% of the amplified products from calculation, showing a maximum value, and the equation below was derived. When the chain length to be extended is determined, it is desirable to carry out PCR reaction in the presence of ddNTP satisfying the following equation:

$$0.95 < \{dNTP \text{ concentration}/(dNTP \text{ concentration} + ddNTP \text{ concentration})\}^a < 0.96$$

(where "dNTP concentration" represents the concentration of deoxynucleotides in the above reaction solution, and "ddNTP concentration" represents the concentration of dideoxynucleotides in the above reaction solution. Further, a represents the number of nucleotides extended in the amplification reaction ($1 \leq a$).)

In the present method, the position where the extension reaction stops in the step of carrying out amplification reaction is unknown, and therefore there is a possibility that amplified products without having a sequence region of a detection target such as polymorphism site and thus without having sequences complementary to the probe are formed. Further, the probability of termination of the extension reaction becomes higher as the chain length becomes longer, resulting in a higher presence ratio of shorter single-stranded nucleic acids. Therefore, it is desirable that at least the labeled primer which is one of the pair of primers used for the amplification reaction is designed so as to anneal adjacently to the target sequence region in order to obtain amplified products with high sensitivity in the step of carrying out amplification reaction.

More specifically, when the detection target is a SNP, the labeled primer is designed such that the position of the 3' end of the primer is separated from the SNP by 5 to 128 nucleotides, preferably 5 to 64 nucleotides, and more preferably 5 to 20 nucleotides. By designing the labeled primer in this way, amplification products that show higher sensitivity can be obtained, thereby further enhancing the sensitivity of the method for detecting a nucleic acid according to the present invention.

Figure 3:
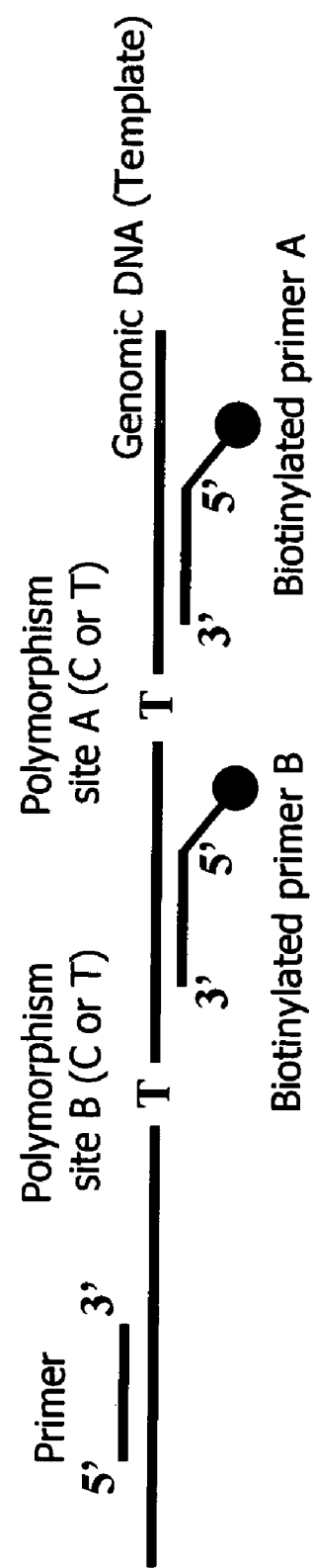
FIG. 3 a schematic drawing to explain a step of carrying out an amplification reaction with the use of an additional primer as another example of the method for detecting a nucleic acid according to the present invention.

On the other hand, the method for detecting a nucleic acid according to the present invention is not limited to the example in which amplification reaction is performed with the use of a pair of primers as described above, and for example, another example in which the amplification reaction is performed with the use of additional primers in addition to the pair of primers is also applicable as described below. When a plurality of target sequence regions are present in amplified products, the additional primers are designed to anneal adjacently to each of the target sequence regions. More specifically, when target polymorphism sites A and B are present in the nucleic acid serving as a template as shown in FIG. 3, "a primer" and "a biotinylated primer A" in FIG. 3 are prepared as the pair of primers. Further, a biotinylated primer B is prepared as the additional primer in this instance. The biotinylated primer B is designed such that its Tm value becomes lower compared with that of the biotinylated primer A.

In the present method, a reaction solution containing the pair of primers and the additional primer thus designed is prepared, and an amplification reaction is carried out as described above. In the present method, setting of annealing temperature in the amplification reaction is gradually lowered after each step of the cycle. Alternatively, the setting may be lowered stepwise. In this way, amplification reactions proceed preferentially from the pair of primers during the initial steps of the cycles, while extension reactions proceed from the additional primer as well in the later steps of the cycles. By performing the amplification reactions under these settings, amplified products containing all target sequence regions for detection can be efficiently obtained, even though a plurality of target sequence regions for detection are present in the amplified products.

Figure 4:
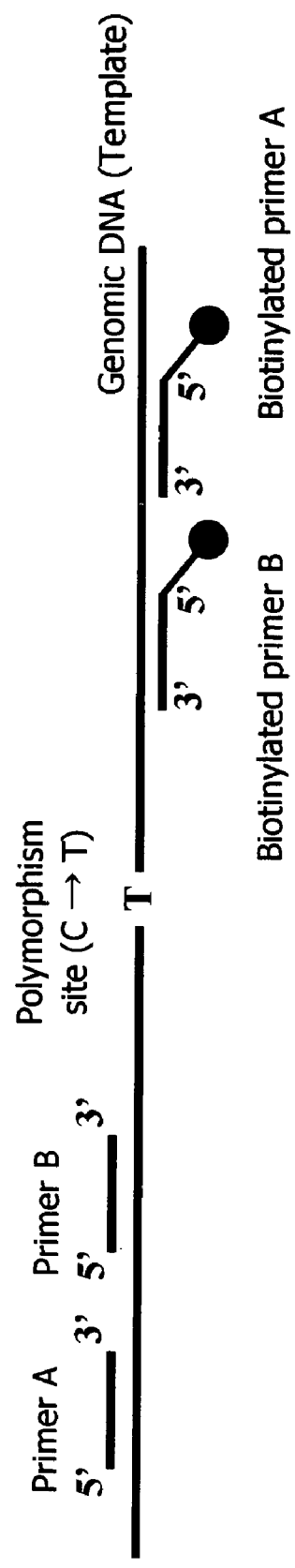
FIG. 4 is a schematic drawing to explain a step of carrying out an amplification reaction with the use of a plurality of primer pairs as still another example of the method for detecting a nucleic acid according to the present invention.

Furthermore, the method for detecting a nucleic acid according to the present invention is not limited to the example in which amplification reaction is performed with the use of a pair of primers, and for example, another example in which the amplification reaction is performed with the use of a plurality of primer pairs is also applicable as described below. In the example in which the amplification reaction is performed with the use of a plurality of primer pairs, as shown in FIG. 4 for example, "a primer A" and "a biotinylated primer A" as well as "a primer B" and "a biotinylated primer B" are prepared as the primary pair of primers and the secondary pair of primers, respectively. The secondary pair of primers is designed such that these Tm values become lower compared with those of the primary pair of primers.

In this method, a reaction solution containing the two pairs of primers thus designed is prepared, and an amplification reaction is carried out as described above. At this time, in the present method, setting of annealing temperature in the amplification reaction is gradually lowered after each step of the cycle. Alternatively, the setting may be lowered stepwise. In this way, amplification reactions proceed preferentially from the primary pair of primers during the initial steps of the cycles, while amplification reactions proceed from the secondary pair of primers as well in the later steps of the cycles. By performing the amplification reactions under these settings, non-specific amplification reaction can be prevented. Furthermore, since the amplification reactions are performed at lower temperatures in the later steps of the cycles, it is possible to increase the amount of amplified products. Still further, the fact that the amplification takes place also from the secondary primers designed for the internal sequence results in amplification from two pairs of primers, thereby giving rise to more sequence-specific amplification reactions.

EXAMPLES

Hereinafter, the present invention is explained in more detail with reference to examples. However, the technical scope of the present invention is not limited to the following examples.

1) Purpose

The purpose is to prepare labeled single-stranded DNAs from a genome and the like without being inhibited from obtaining amplification products stably, and to demonstrate ultimately an effect of enhancement in detection sensitivity.

2) Principle

In the present example, gene amplification was carried out by the polymerase chain reaction (PCR) using a genomic DNA as a template. Then the amplified products were hybridized to a probe immobilized to a carrier, and measurement of the presence and absence of the hybridization was carried out with the reverse sequence-specific oligonucleotide (rSSO) method for detection of a mutation.

3) Materials

In the present example, an aldehyde dehydrogenase gene was used as the template DNA. The target mutation site was a nucleotide at position 1556 of the aldehyde dehydrogenase gene (Accession No. BC002967) of the template DNA. In the present example, a pair of primers was designed to sandwich a genomic sequence of 64-mer containing this mutation site. Specifically, a primer A (Sequence; 3'-AGC CCA GTC ACC CTT TGG TG-5'; Sequence No. 1) and a biotinylated primer B (Sequence; 3'-CTT TGA CTG TGA CAG TTT TC-5'; Sequence No. 2) were used.

As the probe, an oligonucleotide 1 (Sequence; 3'-AGG CAT ACA CTg AAG TGA AA-5'; Sequence No. 3) and another oligonucleotide 2 (Sequence; 3'-AGG CAT ACA CTa AAG TGA AA-5'; Sequence No. 4) that are able to hybridize to the DNA containing the mutation site were used. The carrier for use in binding the probes was Luminex carboxyl-coated beads (product of Hitachi Software Engineering Co., Ltd.). The DNA polymerase used was Taq DNA polymerase (product of Qiagen Inc.). The substrates for use in the PCR method were dNTP and ddNTP (product of Invitrogen Corporation). The fluorescent substance used was streptavidin-phycoerythrin (SA-PE) (product of Molecular Probes Corporation).

4) Measurement System

The Luminex system (Manufactured by Hitachi Software Engineering Co., Ltd.) was used for measurement in the present example. The Luminex system allows a plurality of items to be measured at a time owing to the use of special beads as the carrier. The special carrier is made of polystyrene in a diameter of ca. 5.6 μm and dyed with a plurality of fluorescent substances. By changing the contents of these fluorescent substances, differential measurements are possible by the differences in coloring even if these are present in the same solution. Different biopolymers such as antibody and nucleic acid are bound to these beads, respectively, thereby allowing the presence or absence of biopolymers that can interact with those biopolymers to be measured. Namely, this system is characterized in that measurement of multiple items is possible with high sensitivity even for a small amount of sample.

5) Method (1) Amplification of Genomic Sequence

Amplification is carried out for a genomic DNA as a template using the primer A and the biotinylated primer B. In the present example, dNTP and ddNTP were used as the substrates for amplification by PCR, and their content ratios were changed, thereby evaluating the significance of the use of ddNTP. In practice, the evaluation was performed at ratios of ddNTP to the total substrate amount of 0/10,000, 1/10,000, 2/10,000, 3/10,000, 4/10,000, 5/10,000, 6/10,000, 7/10,000, 8/10,000, 9/10,000, 10/10,000, 15/10,000, and 20/10,000, respectively. All other conditions were identical to one another, and the amplification reactions in which one cycle was run at 94 degrees C. for 30 sec, 65 degrees C. for 30 sec, and 72 degrees C. for 30 sec were carried out for 30 cycles.

(2) Hybridization between Amplified Products and Probes

The obtained amplified products and the probe immobilized to Luminex beads were subjected to thermal denaturation and hybridization at 94 degrees C. for 2 min and 50 degrees C. at 30 min, respectively.

(3) Fluorescence Measurement by Luminex System

After removing unhybridized amplified products and biotinylated primer B by washing and the like, the hybridized amplified products were fluorescently labeled with SA-PE, followed by measurement of fluorescence values by the Luminex system.

6) Results

Figure 5:
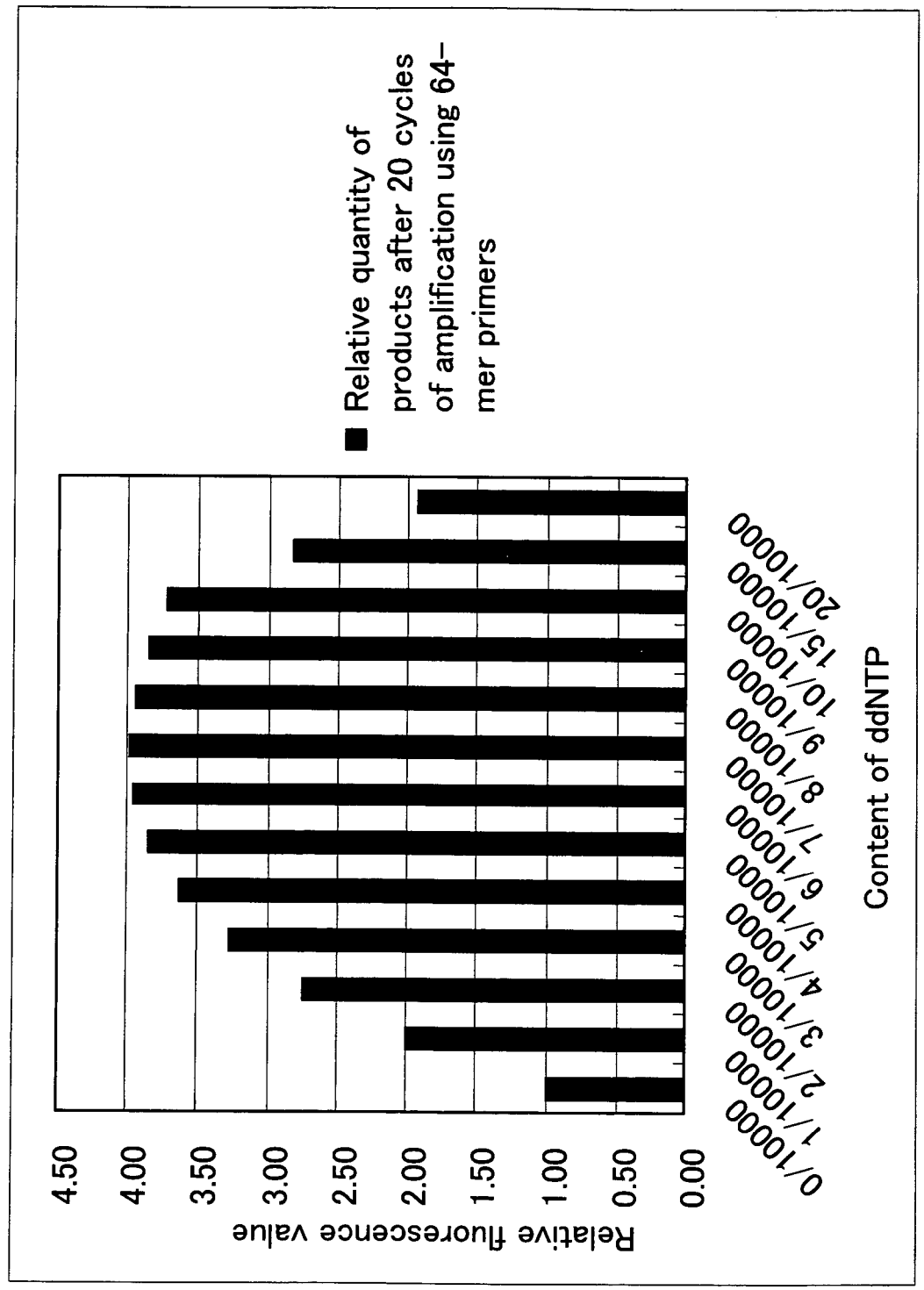
FIG. 5 is a characteristic graph to show the relation between the content of dideoxynucleotides and the value of relative fluorescence obtained from the results of an example.

The obtained results are summarized in FIG. 5 and shown in a bar graph assuming that the fluorescence value without the use of ddNTP is one. An approximately 4-fold increase in fluorescence can be obtained by adjusting the content of ddNTP.

What is claimed is:

1. A method for detecting a nucleic acid, comprising the steps of:

carrying out amplification reaction to amplify a predetermined region of the nucleic acid in a reaction solution comprising the nucleic acid acting as a template, a pair of primers, deoxynucleotides, and dideoxynucleotides;

hybridizing amplified products of the reaction solution to a probe; and detecting the hybridization between the amplified products and the probe; and wherein the amplification reaction is carried out using a reaction solution in which the concentration ratio of the deoxynucleotides to the dideoxynucleotides meets the equation;

$$0.1 < \{dNTP \text{ concentration}/(dNTP \text{ concentration} + ddNTP \text{ concentration})\}^{ab} \leq 1.0$$

wherein "dNTP concentration" represents the concentration of deoxynucleotides in the reaction solution, "ddNTP concentration" represents the concentration of dideoxynucleotides in the reaction solution, "a" represents the number of nucleotides extended in the amplification reaction ($1 \leq a$), and "b" represents the cycle number of the amplification reaction.

2. The method for detecting a nucleic acid according to claim 1, wherein b in the equation is in the range of $20b \leq 24$.

3. The method for detecting a nucleic acid according to claim 1, wherein either primer of the pair of primers is designed to anneal to a region adjacent to the nucleotide sequence complementary to the probe.

4. The method for detecting a nucleic acid according to claim 1, wherein at least either primer of the pair of primers and/or the probe is labeled in advance.

5. The method for detecting a nucleic acid according to claim 1, wherein the amplification reaction is carried out using the reaction solution that comprises at least one additional primer having a lower Tm value compared with those of the pair of primers.

6. The method for detecting a nucleic acid according to claim 1, wherein the temperature of annealing in the amplification reaction is set lower after each amplification cycle.

7. The method for detecting a nucleic acid according to claim 1, wherein the amplification reaction is carried out using the reaction solution that comprises a pair of secondary primers having lower Tm values compared with those of the pair of primers.

* * * * *